(12) United States Patent
Grant et al.

(10) Patent No.: US 6,387,040 B1
(45) Date of Patent: *May 14, 2002

(54) URINARY CONTINENCE DEVICE AND METHODS FOR URINARY CONTROL

(75) Inventors: Robert C. Grant, New Hope; Sidney F. Hauschild, St. Paul; Mark Polyak, Minnetonka, all of MN (US)

(73) Assignee: American Medical Systems, Inc., Minnetonka, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/499,158

(22) Filed: Feb. 7, 2000

Related U.S. Application Data

(62) Division of application No. 09/126,670, filed on Jul. 30, 1998, now Pat. No. 6,030,337.

(51) Int. Cl.[7] .............................. A61F 2/00; A61F 5/48
(52) U.S. Cl. ...................................... 600/29; 128/885
(58) Field of Search .............. 600/29–32; 604/327–328, 604/249, 99.02; 128/DIG. 25, 885

(56) References Cited

U.S. PATENT DOCUMENTS

| | | | | |
|---|---|---|---|---|
| 4,457,299 A | * | 7/1984 | Cornwell | 600/29 |
| 5,114,398 A | * | 5/1992 | Trick et al. | 600/29 |
| 5,562,599 A | * | 10/1996 | Beyschlag | 600/29 |
| 5,722,931 A | * | 3/1998 | Heaven | 600/29 |
| 6,030,337 A | * | 2/2000 | Grant et al. | 600/29 |

* cited by examiner

Primary Examiner—John P. Lacyk
Assistant Examiner—Michael Astorino
(74) Attorney, Agent, or Firm—Oppenheimer Wolff and Donnelly LLP

(57) ABSTRACT

A design and method of manufacture are disclosed for a female continence augmentor device used to alleviate urinary incontinence. The female continence augmentor includes a mount formed of a resilient material, an intralumenal part carried on the mount and a resilient portion carried on the intralumenal part of device. The mount adheres to the female body about the urethral exit to support the female augmentor into position to prevent inadvertent urine loss. The intralumenal part of the device extends from the mount into the urethral lumen at least to the mid-urethra. In particular, the resilient portion of the intralumenal part extends into the urethra and is adapted to at least urge the dorsal urethral wall in the dorsal direction to stretch and/or reshape the mid-urethral lumen to have a more arcuate shape. Thus, the mid-urethral lumen in cross-section would preferably exhibit a crescent shape of smaller radius. As such, the female continence augmentor enables a patient to void voluntarily with normal muscle control and without requiring conscious action to operate the device. Following voiding, the continence augmentation function of the device resumes automatically thereby increasing urethral resistance to opening and preventing inadvertent urine loss.

18 Claims, 10 Drawing Sheets

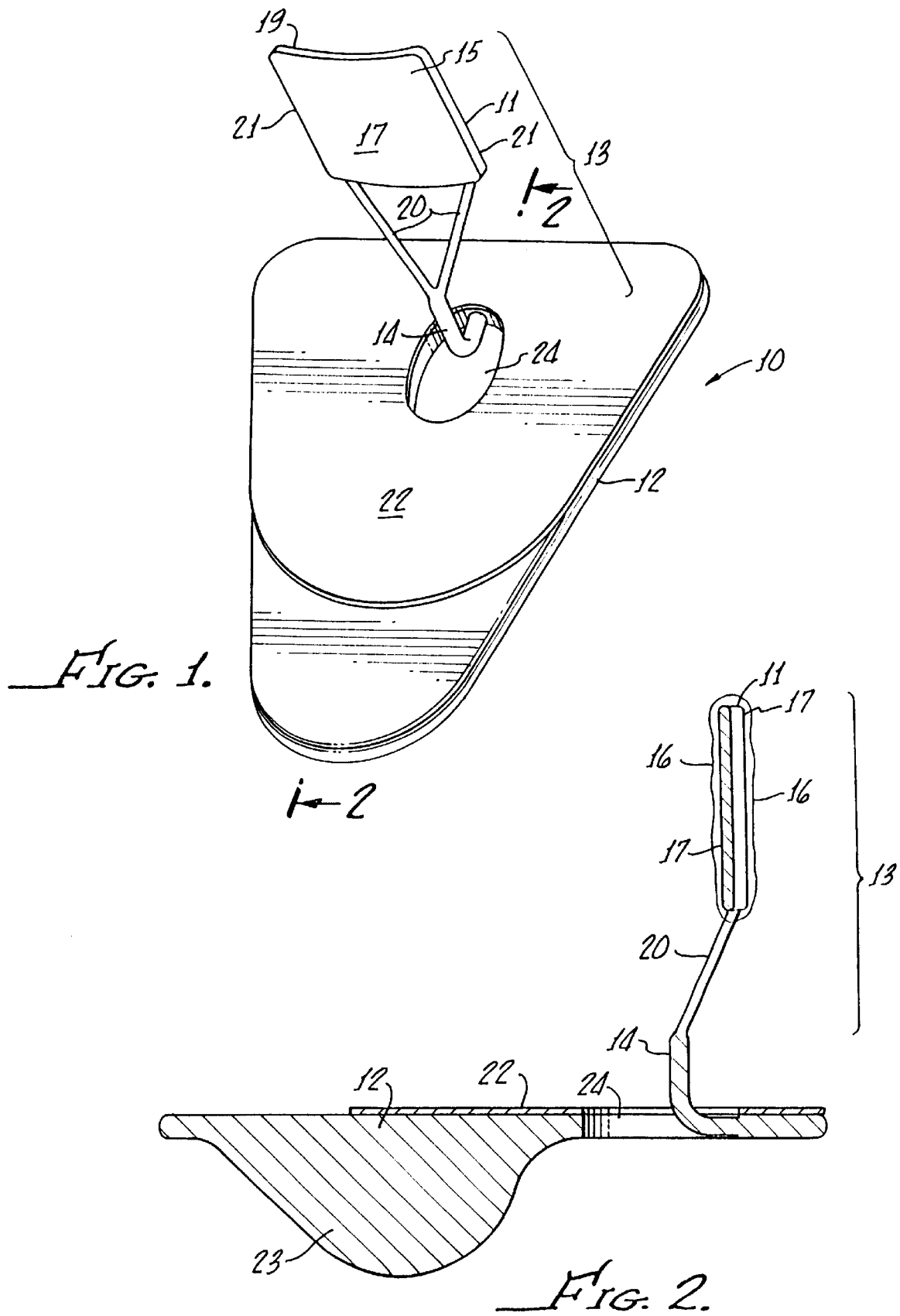

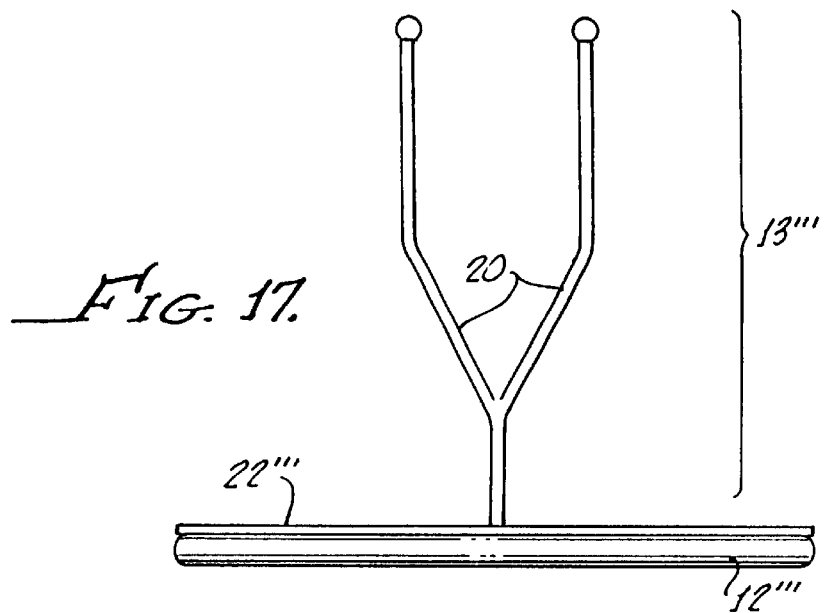
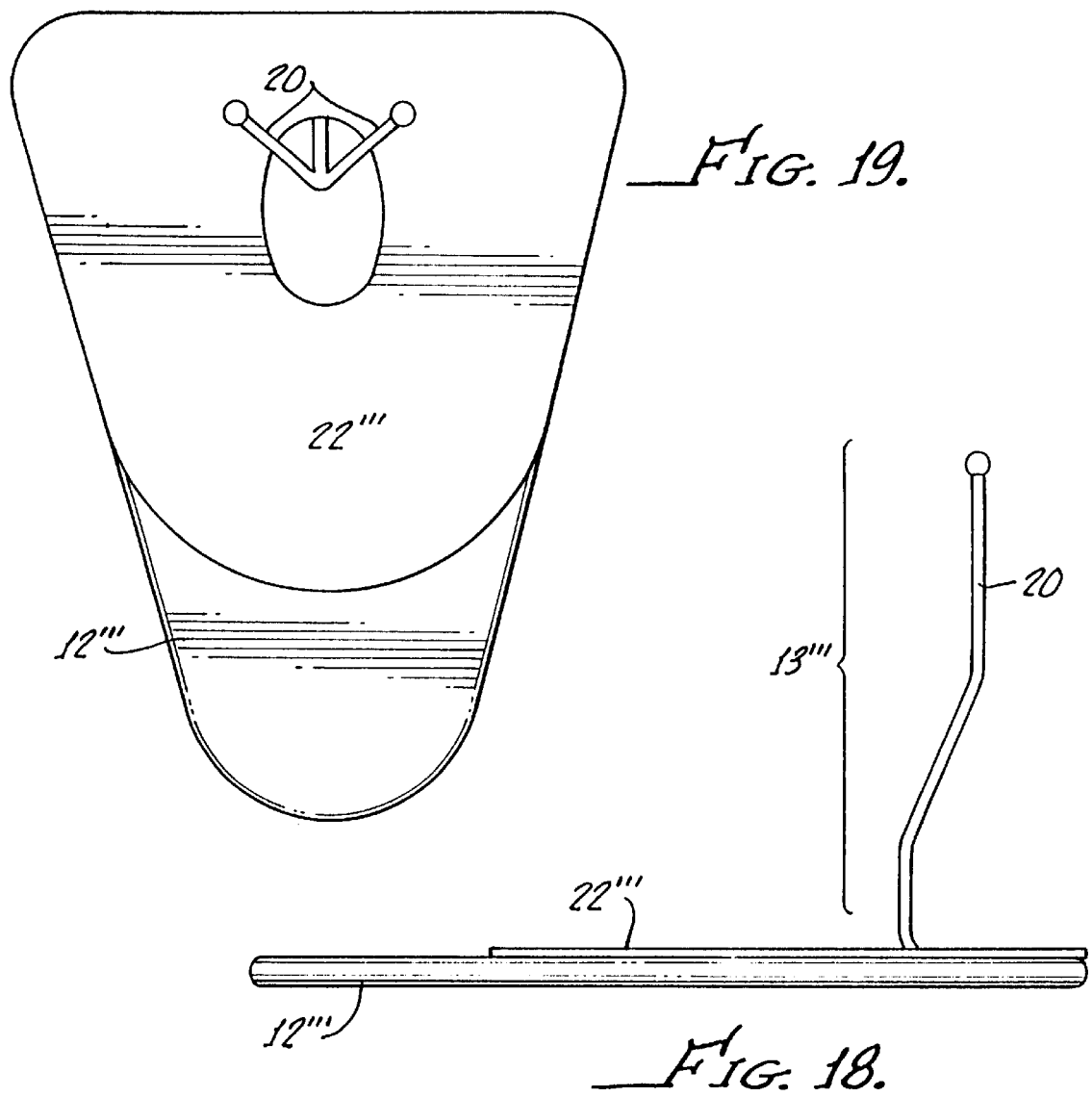

URINARY CONTINENCE DEVICE AND METHODS FOR URINARY CONTROL

CROSS-REFERENCE TO RELATED APPLICATIONS

This is a divisional application of U.S. patent application Ser. No. 09/126,670, filed Jul. 30, 1998, now U.S. Pat. No. 6,030,337 entitled CONTINENCE AUGMENTOR AND METHODS FOR URINARY CONTROL.

BACKGROUND OF THE INVENTION

Urinary incontinence, which is a condition involving involuntary loss of urine, is a problem with millions of people. It is much more prevalent among women than men. In some patients, loss of urine is associated with transient increases in intra-abdominal pressure that result from activities such as coughing, sneezing, lifting, straining, exercise and in severe cases, even simply changing body position. This is called stress incontinence.

The normal urinary continence mechanism combines contributions from several components including muscles in and around the urethra, blood pressure in the urethral vascular plexus between the smooth muscle in the urethral wall and the epithelial lining, the mucosal seal between the walls of the closed urethral lumen (coaptation), and support from endopelvic fascia. During urination the muscles in and around the urethra relax and the bladder muscle (the detrusor) contracts. Fluid pressure from the bladder overcomes the mucosal seal, the lumen opens and urine is expelled.

While the bladder is filling, increases in bladder pressure normally induce reflex reactions in the muscles of the continence system to increase urethral closure pressure. This reflex response is normally adequate to prevent involuntary urine loss. If the resistance to urethral opening is insufficient to keep the lumen sealed, the female patient experiences episodes of stress incontinence. Stress incontinence results from inadequate functioning of one or more of the components of the normal continence system.

Options currently available for management of female urinary stress incontinence include the use of externally applied absorbent products, pelvic muscle exercises, electrical stimulation of pelvic muscles, devices that occlude the urethra either internally or externally at the urethral meatus, and injections that add bulk to the urethral wall and surgery. A number of external and internal female continence devices have been patented.

U.S. Pat. No. 5,074,855 discloses a device for controlling urinary incontinence in a human female including a resilient pad configured to seal against and occlude the urethral meatus of the user. A similar device is disclosed in U.S. Pat. No. 5,336,208. In those devices, an adhesive is provided to seal the body of the device against the urethral meatus.

International Applications No. 96/39989, 96/39990 and 96/39991 each disclose a female urinary incontinence device in the form of an urethral cap with a partially deformable body portion, a hand gripping portion and a body contacting surface. The body portion defines a chamber which allows for a vacuum seal when applied to the patient's body.

U.S. Pat. No. 5,082,006 has a shaft to be inserted into the urethra and one or more knobs on the shaft to plug the passage of urine therethrough. A flap on the proximal end of the shaft holds the positioning of the shaft in the urethra.

Each of the above devices prevents urinary loss by occluding the internal or external urethral orifice and each has to be removed by the patient to allow micturition.

It is desirable to have a device which satisfactorily prevents urinary loss and also permits voluntary voiding without needing to remove the device from the body of the patient. It has now been found that these benefits may be achieved with a female continence augmentor that prevents involuntary urine loss while allowing urine flow during voluntary micturition. The female continence augmentor, described herein, achieves the desired effects by gently stretching and reshaping the midurethra from within its lumen, Stretching the perimeter of the lumen increases tension in the surrounding midurethral wall bringing the opposing surfaces of the epithelial lining into more intimate contact for enhancing coaptation. Coupled with the action of the regular continence mechanism, the increased tension and improved coaptation make the urethra more resistant to dilation by urine during transient increases in abdominal pressure, thus relieving stress incontinence.

When the user of the female continence augmentor wishes to void, the muscles of her continence mechanism relax, reducing tension in the urethral wall sufficiently to permit dilation of the lumen under normal bladder pressure. The female continence augmentor acts as a spring, exerting force directly proportional to the compressive force applied by the muscles of the continence mechanism. When the continence mechanism relaxes, the force from the augmentor drops to a level that does not significantly increase the fluid pressure required to dilate the urethra for urination. The female continence augmentor maintains contact with the dorsal midurethral wall at all times, but the reduced muscular tension allows urine pressure to stretch the urethra, opening a slit-shaped passage for urine between the ventral urethral wall and the ventral surface of the augmentor.

When voiding is complete, contraction of the sphincteric muscles restores tension in the urethral wall and the female continence augmentor resumes functioning automatically. Thus, the female continence augmentor functions through dynamic interactions with the biological continence mechanism. Its mode of action is clearly different than that of previous intraurethral continence devices, which act as plugs that must be removed or plugs with valves that must be externally activated for voiding.

SUMMARY OF THE INVENTION

The female continence augmentor adapted to prevent involuntary urine loss due to transient increases in bladder pressure but to passively allow urine flow during voluntary emptying of the bladder. The female continence augmentor improves urethral coaptation and increases mid-urethral resistance to opening the lumen while the bladder is filling. The female continence augmentor preferably has a mount formed of a resilient material. The mount most preferably adheres to the female body about the urethral exit to support the female continence augmentor in position to prevent inadvertent urine loss through the midurethral lumen. The mount may perhaps include a layer of adhesive applied thereto and the adhesive might be adapted to releasably attach to the female body.

An intralumenal part may be carried on the mount. The intralumenal part preferably includes a resilient portion carried on the mount. The resilient portion can extend into the urethra and could be adapted to at least urge the dorsal midurethral wall in a dorsal direction to stretch and/or reshape the midurethral lumen to have a more arcuate shape transversely thereacross. Thus the midurethral lumen in cross section would preferably exhibit a crescent shape of smaller radius. The intralumenal part might include two struts or a member attached to one or two struts extending from the resilient portion for stretching, reshaping and repositioning the midurethral lumen intralumenally.

The member might be adapted for engaging the urethral wall, especially the midurethral wall to remove laxity therein and for enhancing coaptation and increasing urethral resistance to opening. The patient may void voluntarily with normal muscle control but otherwise without requiring conscious action to operate the female continence augmentor or needing to remove, activate, inactivate, or alter it. Following voiding, the continence augmentation function resumes automatically by removing laxity in the midurethral lumen.

The member could include a coaptation improver located thereon and in position for and adapted for engagement with the adjacent midurethral walls. It is preferred that the coaptation improver be biocompatible hydrophilic material adapted to coat with mucus and mucosa within the urethra to prevent involuntary urine loss. The member may be or include a flexible membrane of polymeric material. The flexible membrane might have a structural shape of opposed major surfaces with interstices thereacross. The opposed major surfaces are preferably surrounded by an edge and are preferably generally rectangular.

The member is supported by one or two struts which extend from the resilient portion to the member to urge it against the wall of the midurethral lumen. The two struts may preferably spread apart relative to each other so that the two struts are closer to one another at the resilient portion than at the sides of the member.

The member or flexible membrane might be coated across at least its opposed major surfaces with the biocompatible hydrophilic material that cooperatively fills any gaps between the midurethral walls and the member or flexible membrane. The biocompatible hydrophilic material may promote adherence therewithin and therebetween to seal and prevent involuntary urine loss thereacross. The member or flexible membrane is preferably bowed along the edge transverse to its sides for forming a resilient structure bearing against the midurethral walls. The flexible membrane may be formed of a mesh preferably of flexible polymer. The flexible membrane could possibly have an arcuate shape between opposite sides thereof wherein the opposed major surfaces might perhaps be concave and convex generally in accord with the contour of midurethral lumen cross section.

A method of making the female continence augmentor preferably may improve urethral coaptation and increase mid-urethral resistance to opening the lumen. The method of making preferably has the steps of forming the mount of resilient material and perhaps including the intra lumenal part carried on the mount for extending into the urethra and adapted to at least urge the dorsal midurethral wall in a dorsal direction to stretch and/or reshape the midurethral lumen to have a more arcuate shape transversely thereacross to exhibit a smaller radius. The intralumenal part might include a member attached to the resilient portion for stretching, reshaping and repositioning the midurethral lumen intralumenally for at least urging the dorsal midurethral wall in a dorsal direction for stretching and/or reshaping the midurethral lumen to be a more arcuate shape transversely thereacross. The method of making may have the steps of connecting the intralumenal part to the mount and locating one or more struts on the resilient portion in position for placement relative to the mount intralumenally. The method of making could include the step of forming by molding the mount of a polymer material. The method of making might have the step of locating the member on one or more struts connected to the resilient portion. Substituting the flexible membrane between two struts may be a step. The method of making preferably has the steps of adding adhesive to the mount and having biocompatible hydrophilic material on the member or the flexible membrane to increase coaptation.

A method of using the female continence augmentor might have the mount connected to an intralumenal part. The method of using preferably may include the steps of inserting the intralumenal part into the urethra so that the struts or member thereon are within the midurethral lumen. The step of placing the mount adjacent to the urethral exit to retain the struts or the member in the midurethral lumen can be performed. Stretching and/or reshaping the inside of the urethra with the struts or member urged by the resilient portion that is preferably connected between the mount and struts might be a step. The method of using may include steps of urging the dorsal midurethral wall in a dorsal direction for stretching and/or reshaping the midurethral lumen to have a more arcuate shape transversely thereacross and engaging the urethral wall, especially the midurethral wall to remove laxity therein and for enhancing coaptation and increasing urethral resistance to opening. The patient may void voluntarily without requiring conscious action to operate the female continence augmentor. That is, there is no need to remove, activate, inactivate or alter it. Following voiding, the female continence augmentor resumes functioning automatically.

BRIEF DESCRIPTION OF THE DRAWINGS

FIG. 1 is a view in perspective of a female continence augmentor adapted to prevent involuntary urine loss due to transient increases in bladder pressure but to passively allow urine flow during voluntary emptying of the bladder.

FIG. 2 is a plan view in cross section of the female continence augmentor as would be seen along line 2—2 of FIG. 1.

FIG. 17 is a front view of the alternate female continence augmentor of FIG. 15.

FIG. 18 is a side view shown as an elevation of the alternate female continence augmentor.

FIG. 19 is top plan view of the alternate female continence augmentor of FIG. 15.

DETAILED DESCRIPTION OF THE DRAWINGS

Figure 3:
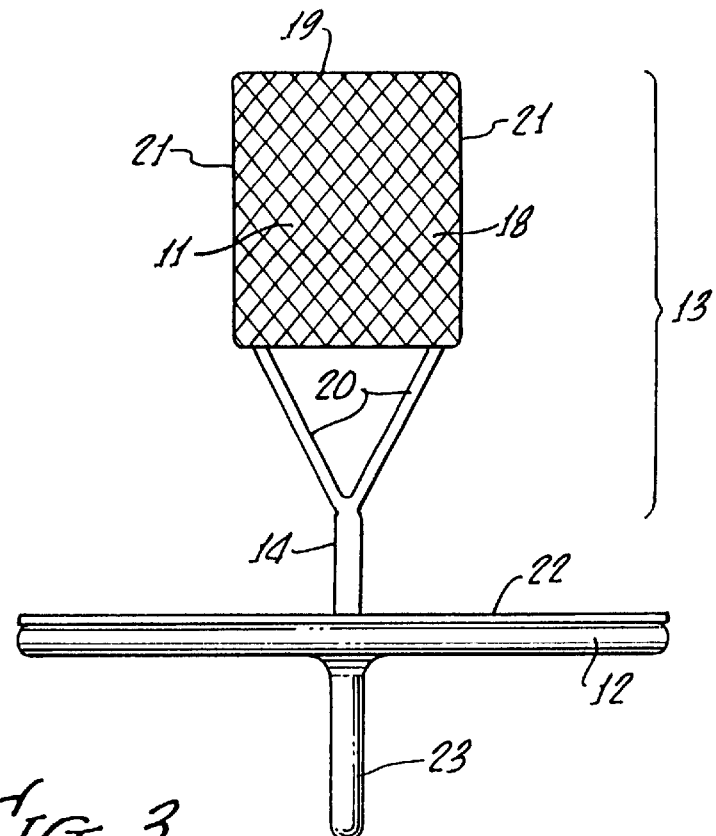
FIG. 3 is a front view of the female continence augmentor of FIG. 1.
Figure 4:
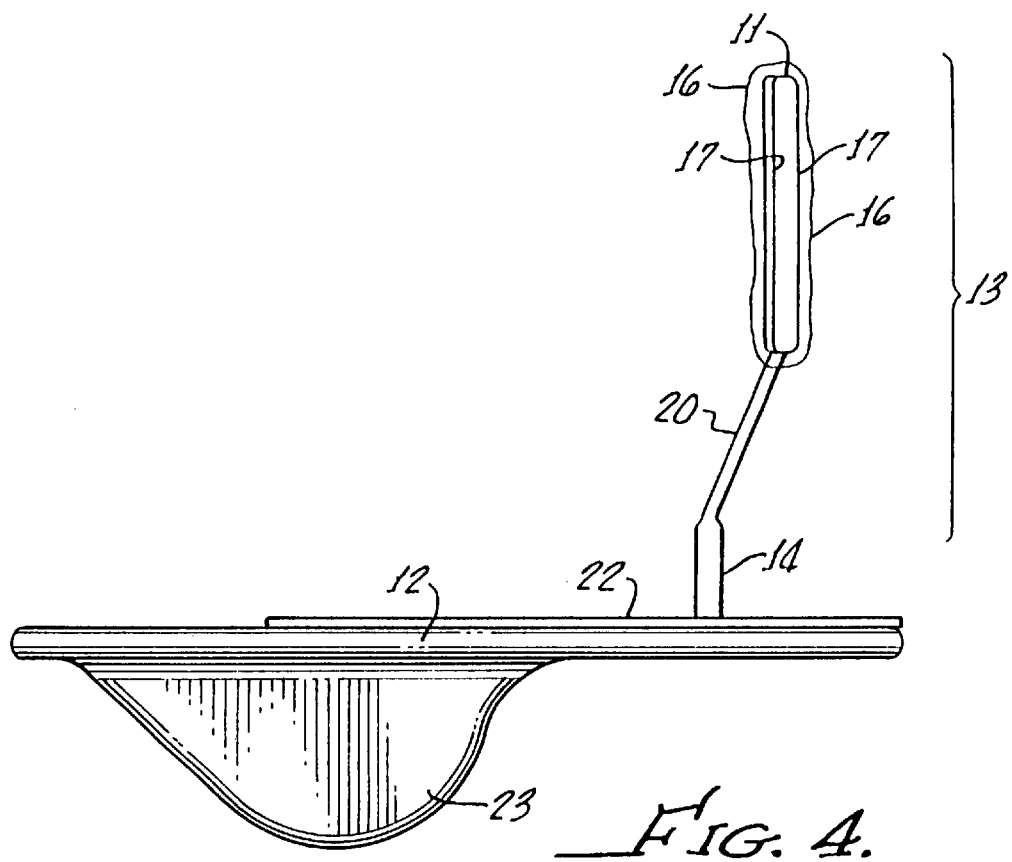
FIG. 4 is a side view shown as an elevation of the female continence augmentor of FIG. 1.
Figure 5:
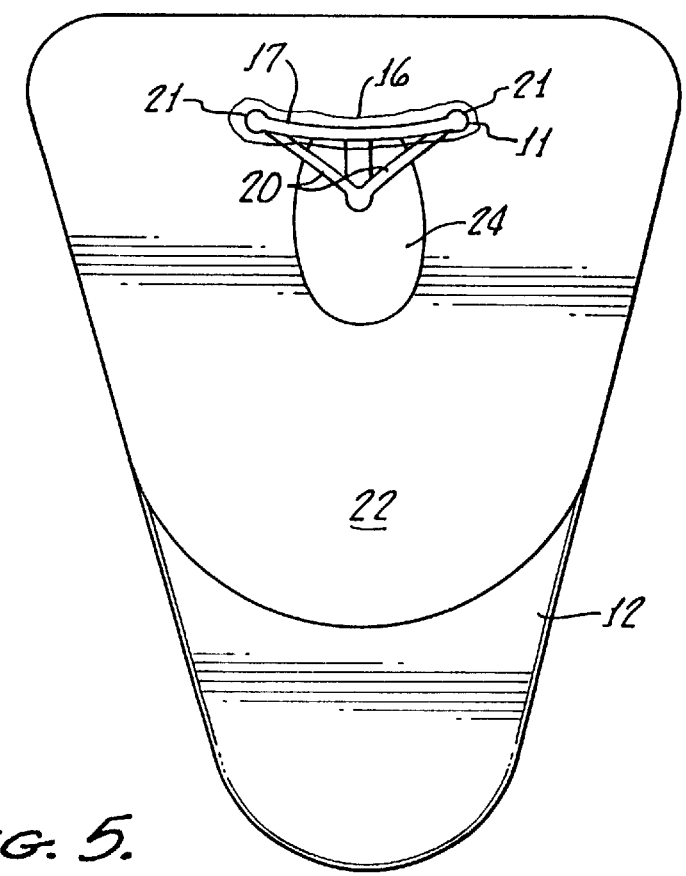
FIG. 5 is top plan view of the female continence augmentor of FIG. 1.
Figure 6:
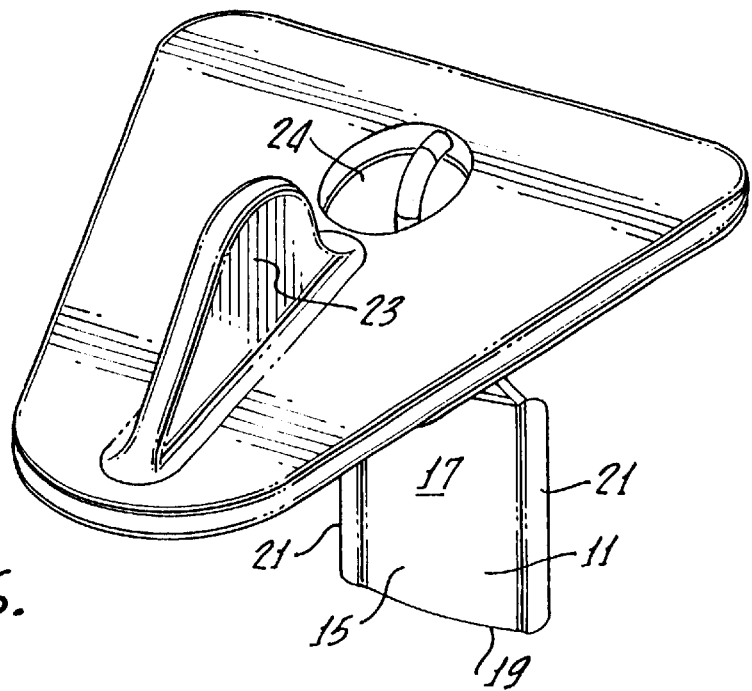
FIG. 6 is a bottom view in perspective of the female continence augmentor of FIG. 1.

Several slightly differing female continence augmentors 10, 10', 10", or 10'" are shown in similar perspective views in the FIGS. 1, 7, 11 and 15, respectively. The reference numbers in each group of Figures for each of the four embodiments disclosed will include identical reference numbers for similar components but for clarity prime numbers will distinguish each of the various embodiments. The female continence augmentor 10, 10', 10" or 10'" is adapted for insertion into a female's midurethral lumen and some have in FIGS. 1, 7, and 11, a flexible membrane 11, 11' or 11" formed of a flexible material. The flexible membrane 11, 11' or 11" may be a formed member 15, 15' or 15" and/or might be assembled from separately made parts. The flexible membrane 11, 11' or 11" is preferably made from a variety of polymer materials that impart the following key characteristics: stability, biocompatability, limited water absorption, very easy and reversible distensibility and compressibility, receptivity to bonding with a surface coating of mucoadhesive. Suitable membranes with these characteristics may be produced from a variety of known polymer materials using molding, casting, extruding, braiding, weaving, knitting or other manufacturing methods that yield the desired characteristics with the polymer selected.

Laxity or slack in the female urethra decreases the resistance of the urethral wall to opening by pressurized urine. This problem is alleviated by the disclosed female continence augmentor 10, 10', 10" or 10'". The female continence augmentor 10, 10', 10" or 10'" is adapted to prevent involuntary urine loss due to transient or unintended increases in bladder pressure but to passively allow urine flow during voluntary or intended emptying of the bladder. The female continence augmentor 10, 10', 10" or 10'" increases midurethral resistance to opening the urethral lumen and improves urethral coaptation. All the female continence augmentors 10, 10', 10" or 10'" have a mount 12, 12', 12" or 12'" formed of a resilient material to accommodate the contours of the female anatomy. The mount 12, 12', 12' or 12'" adheres to the female body about the urethral exit to support the female continence augmentor 10, 10', 10" or 10'" in position to prevent, as explained herein, inadvertent urine loss through the midurethral lumen.

An intralumenal part 13, 13', 13" or 13'" is respectively, carried on the mount 12, 12', 12" or 12'" and is shaped for extending up into the urethra from the mount 12, 12', 12" or 12'". The mount 12, 12' 12" or 12'" adheres about but does not block the urethral exit. The intralumenal part 13, 13', 13" or 13'" also does not block the urethral exit or the urethra connected thereto. The intralumenal part 13, 13', 13" or 13'" includes resilient portion 14, 14', 14" or 14'" extending from the mount 12, 12', 12" or 12'" as best seen in FIGS. 1, 7, 11 or 15 respectively. Thus the resilient portion 14, 14', 14" or 14'" can extend into the urethra in position for at least urging the dorsal midurethral wall in a dorsal direction for stretching and/or reshaping the midurethral lumen to have a more arcuate shape transversely thereacross. That is to say that the resilient portion 14, 14', 14" or 14'" pushes the inside dorsal or back wall of the urethra toward the vagina.

Figure 7:
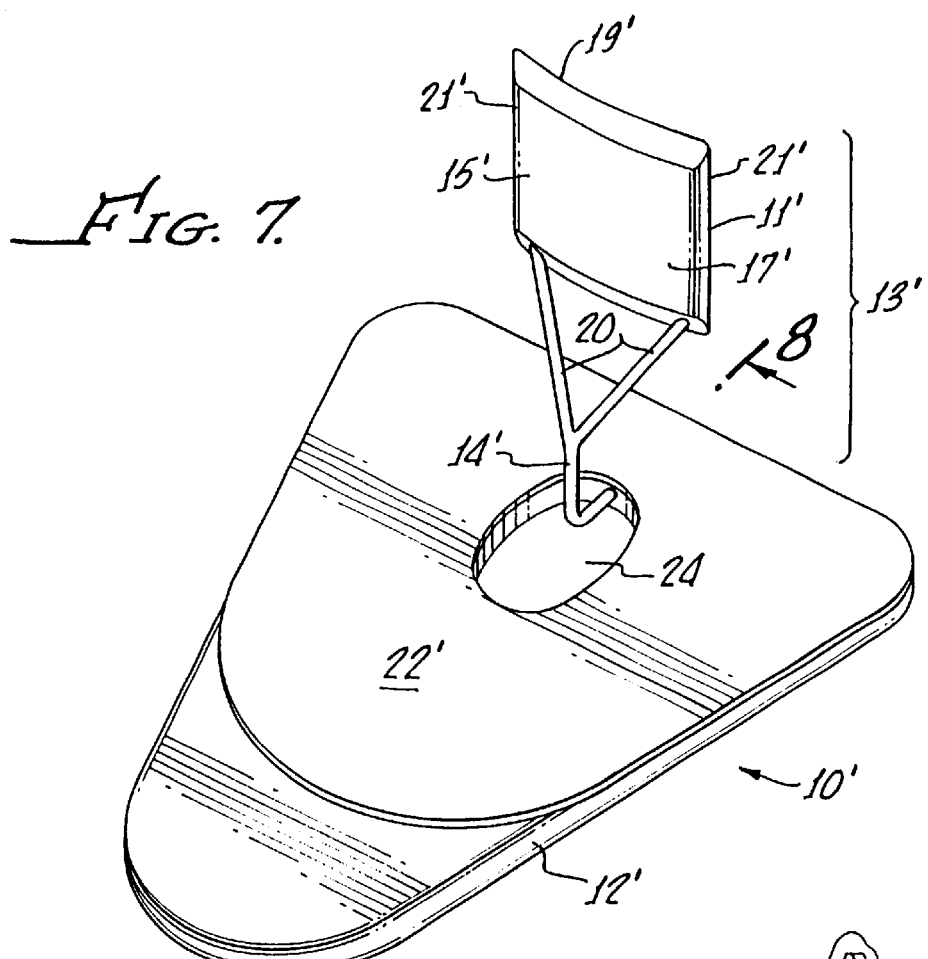
FIG. 7 is a top view in perspective of an alternative female continence augmentor adapted to prevent involuntary urine loss due to transient increases in bladder pressure but to passively allow urine flow during voluntary emptying of the bladder.
Figure 8:
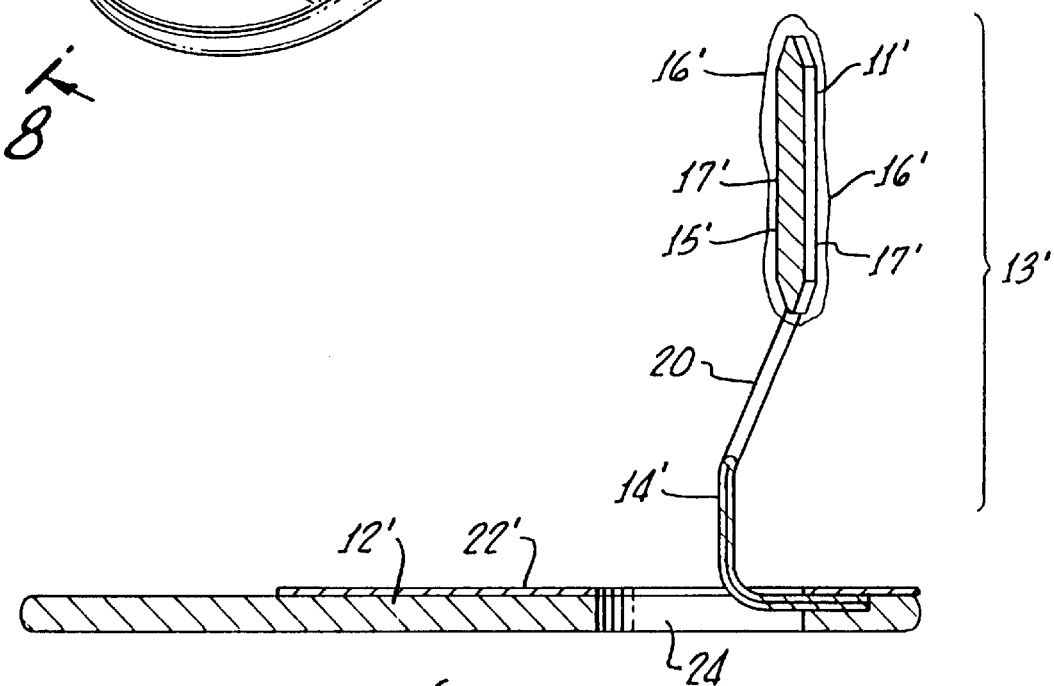
FIG. 8 is a plan view in cross section of the alternative female continence augmentor as would be seen along line 8—8 of FIG. 7.
Figure 9:
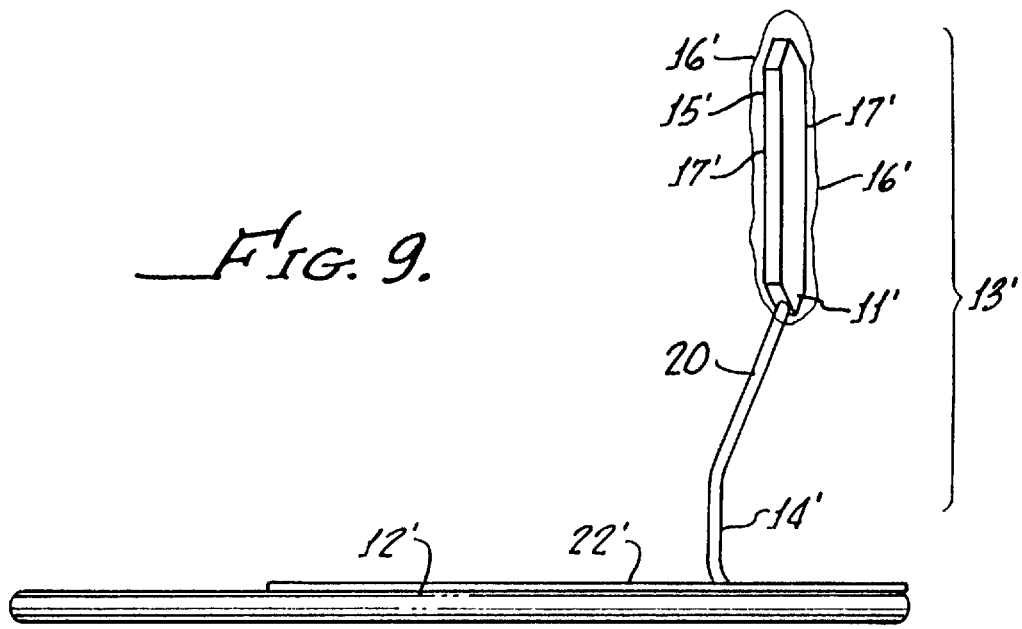
FIG. 9 is a side view shown as an elevation of the alternative female continence augmentor of FIG. 7.
Figure 10:
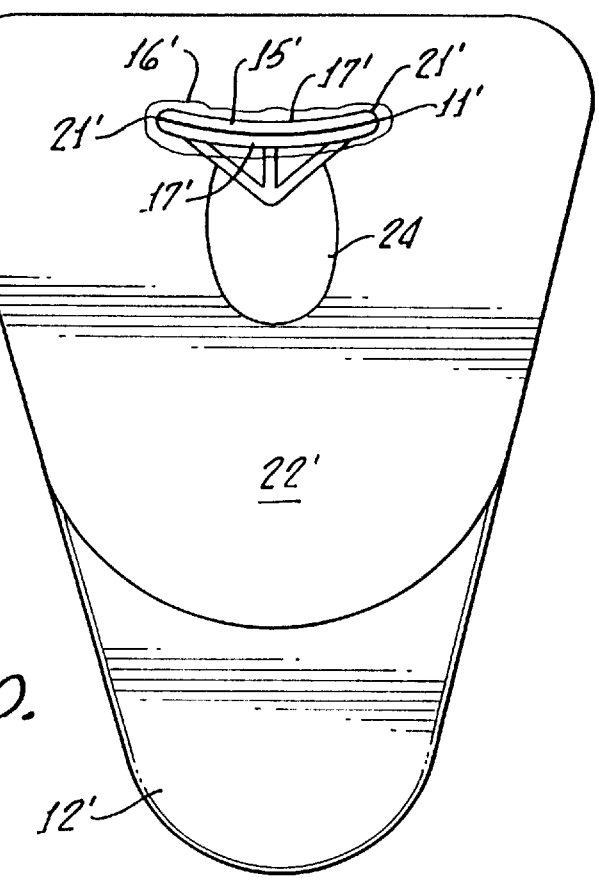
FIG. 10 is an enlarged top plan view of the alternative female continence augmentor of FIG. 7.
Figure 11:
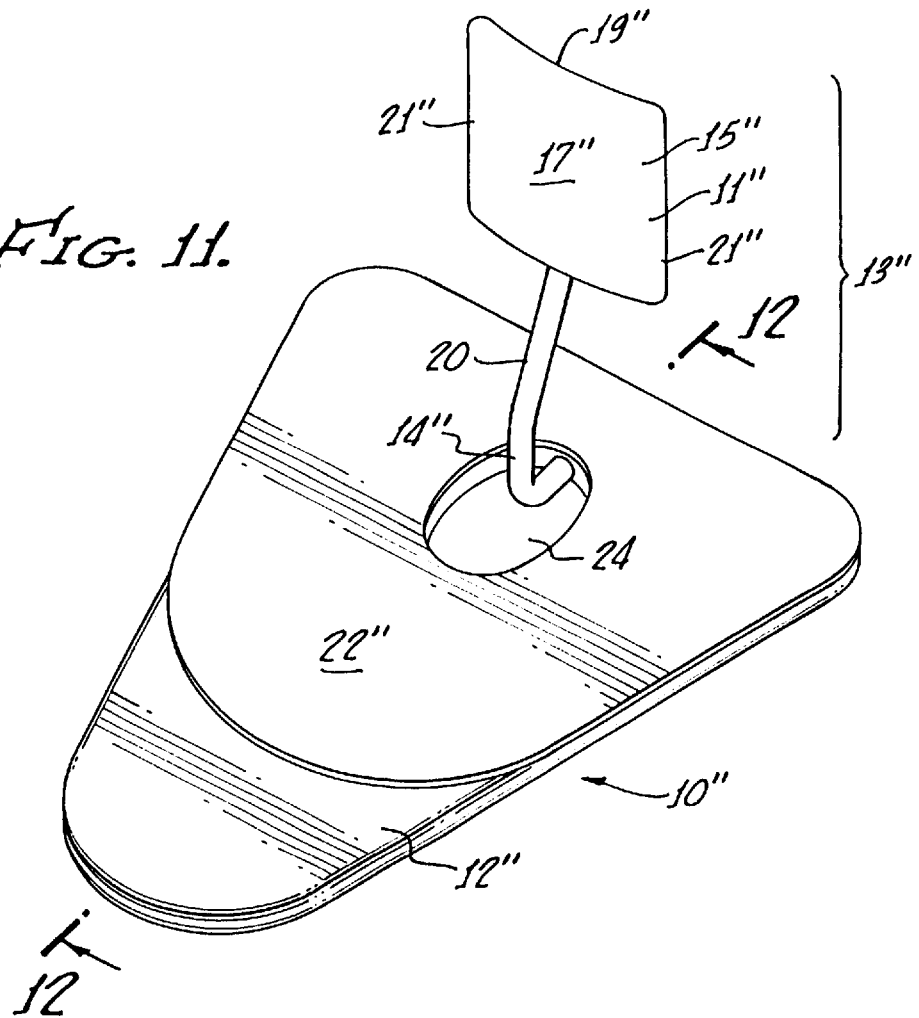
FIG. 11 is a view in perspective of an optional female continence augmentor adapted to prevent involuntary urine loss due to transient increases in bladder pressure but to passively allow urine flow during voluntary emptying of the bladder.
Figure 12:
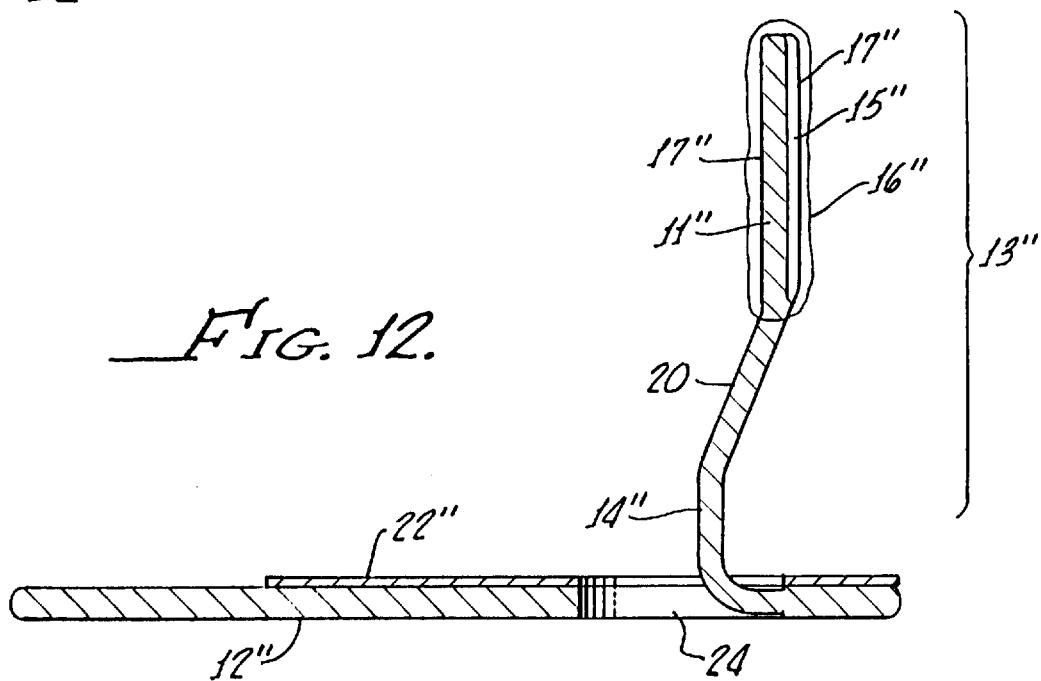
FIG. 12 is a plan view in cross section of the optional female continence augmentor as would be seen along line 12—12 of FIG. 11.
Figure 13:
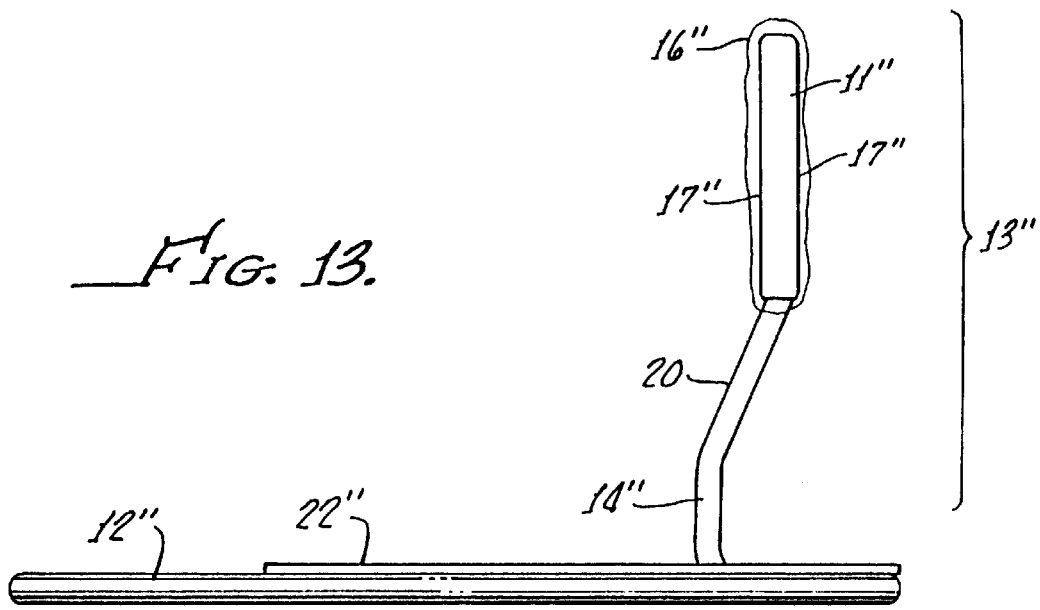
FIG. 13 is a side view shown as an elevation of the optional female continence augmentor of FIG. 11.
Figure 14:
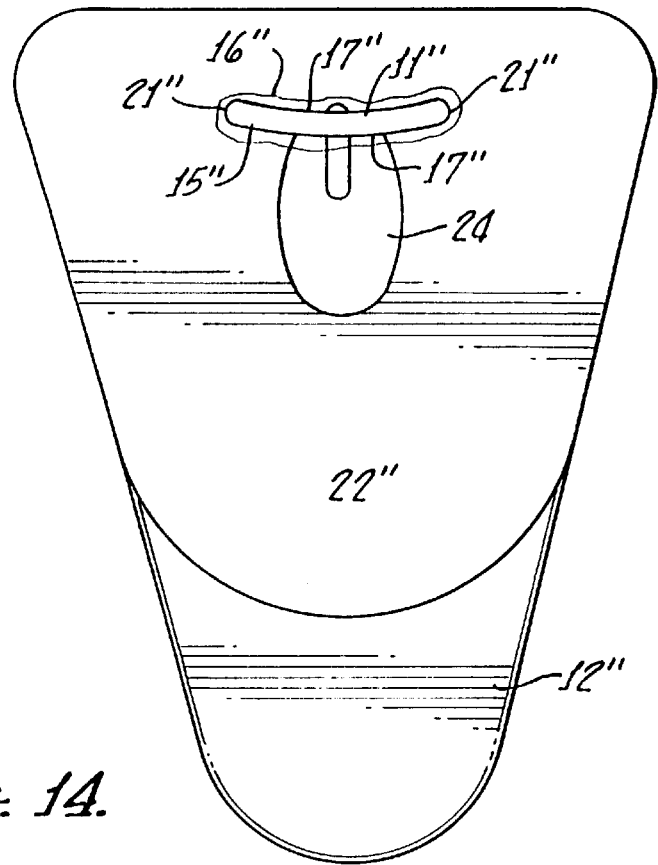
FIG. 14 is top plan view of the optional female continence augmentor of FIG. 11.

The intralumenal part 13, 13' or 13" in FIGS. 1, 7 and 11 includes the member 15, 15' or 15" attached to the resilient portion 14, 14' or 14" for positioning intralumenally in the midurethral lumen. Thus the resilient portion 14, 14' or 14" carries its respective member 15, 15' or 15" in the urethra located for engaging the urethral wall, particularly the midurethral wall to remove laxity therein and for enhancing coaptation and increasing urethral resistance to opening. The patient may void voluntarily without requiring conscious action to operate the female continence augmentor 10, 10', 10" or 10'" or needing to remove, activate, inactivate, or alter it. Bladder pressure will, during voiding, expand the urethra permitting urine to pass the female continence augmentor 10, 10', 10" or 10'". When voiding is completed the continence augmentation function resumes automatically.

The flexible membrane 11, 11', or 11" or the member 15, 15' or 15" may be coated with a coaptation improver 16, 16' or 16", see FIGS. 1 to 14, located on flexible membrane 11, 11', or 11" or the member 15, 15' or 15" in a position for and adapted for engagement with the adjacent midurethral walls. It is preferred that, the coaptation improver 16, 16' or 16" carry biocompatible hydrophilic material, such as mucopolysaccharides, mucoadhesives, dextrans, fruit pectins, polyethers, polyacrylate and its derivatives, polyacrylonitrile and its derivatives, homopolysaccharides, heteropolysacchrides and their derivatives. The biocompatible hydrophilic material coaptation improver 16, 16' or 16" is adapted to coat with mucus and mucosa within the urethra to prevent involuntary urine loss. The flexible membrane 11, 11' or 11" may be coated across at least its opposed major surfaces 17, 17' or 17" with the biocompatible hydrophilic material coaptation improver 16, 16' or 16" that cooperatively fills any space between the midurethral walls and the flexible membrane 11, 11' or 11" or the member 15, 15' or 15" to promote adherence therebetween to seal and prevent involuntary urine loss thereacross.

The formed member 15, 15' or 15" might be made as the flexible membrane 11, 11' or 11" having a length and thickness of about 12 to 15 mm by 0.5 to 1.0 mm, The flexible membrane 11, 11' or 11" or the member 15, 15' or 15" has opposed major surfaces 17, 17' or 17" and perhaps with interstices 18 thereacross as shown only in FIG. 3, for example; although, any of the iterations may have interstices 18. The opposed major surfaces 17, 17' or 17" are surrounded by an edge 19, 19', or 19". The opposed major surfaces 17, 17' or 17" are preferably generally rectangular in shape but arcuate and as such are suitable for the midurethral lumen. The edge 19, 19' or 19" may be beveled, as shown in FIGS. 7 to 10, to enhance the continuity of coaptation along the upper and lower edges of the flexible membrane 11, 11' or 11" or member 15, 15' or 15".

Figure 15:
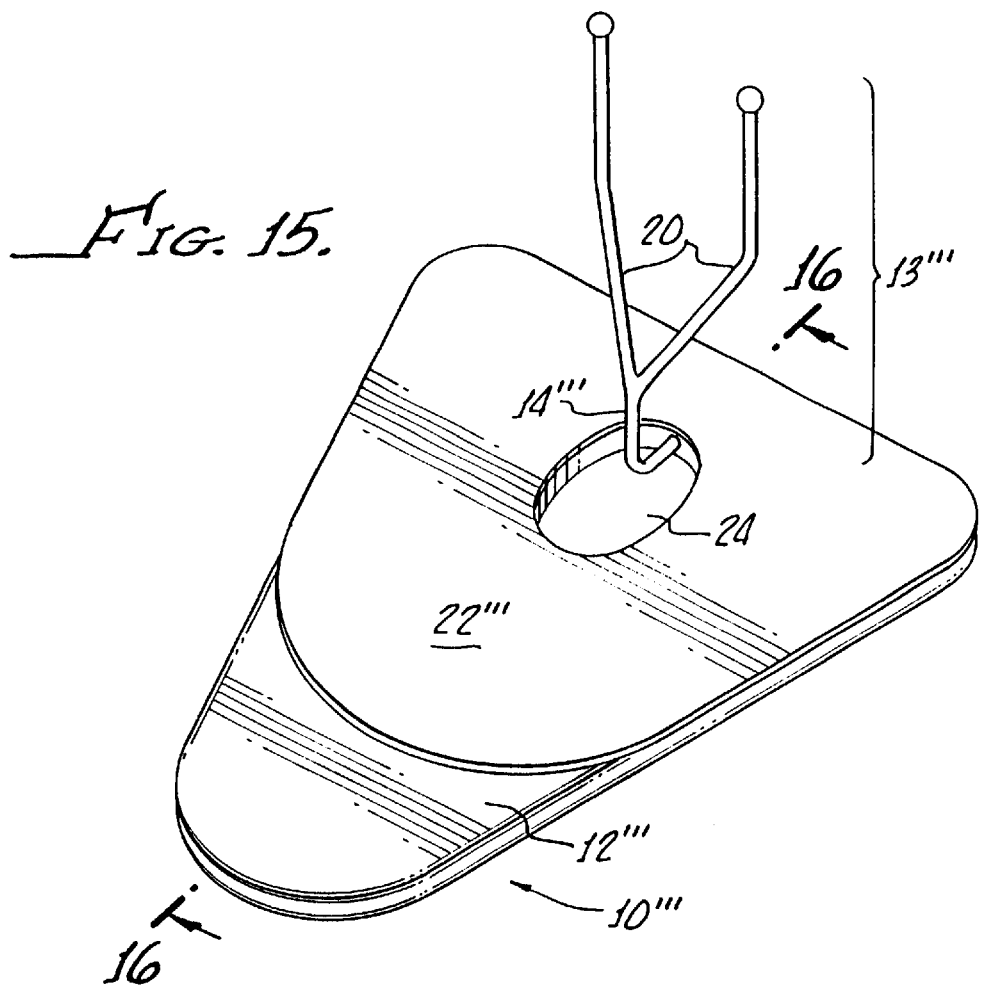
FIG. 15 is a view in perspective of an alternate female continence augmentor adapted to prevent involuntary urine loss due to transient increases in bladder pressure but to passively allow urine flow during voluntary emptying of the bladder.
Figure 16:
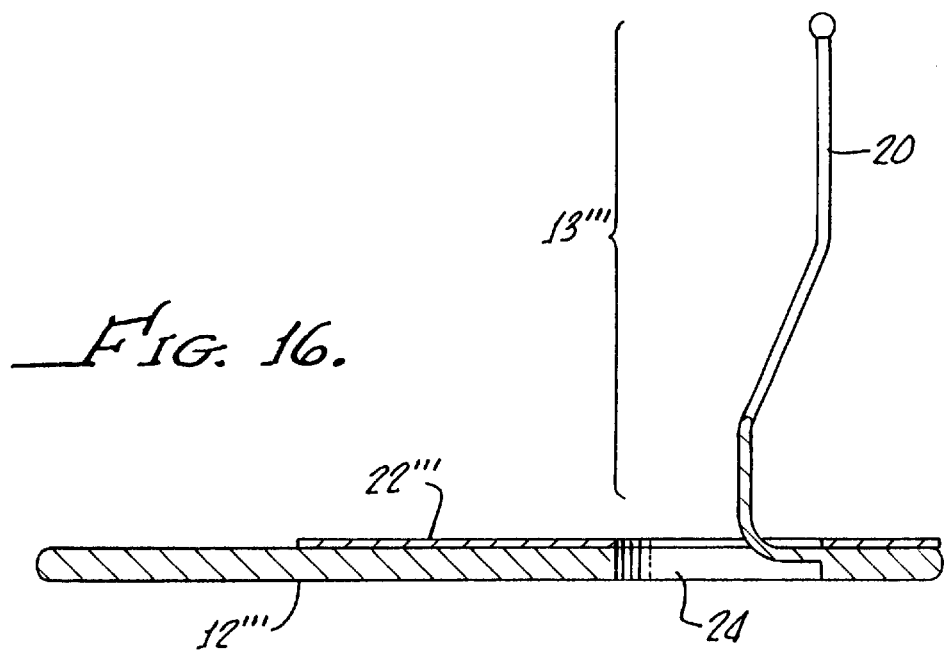
FIG. 16 is a plan view in cross section of the alternate female continence augmentor as would be seen along line 16—16 of FIG. 15.

One or two struts 20 extend from the resilient portion 14, 14' or 14" to the flexible membrane 11, 11' or 11" or member 15, 15' to urge the flexible membrane 11, 11' or 11" or member 15, 15' or against the walls of the midurethral lumen to remove laxity. When two struts 20 are used they extend from opposite sides 21, 21' or 21" of the edge 19, 19' or 19" of the flexible membrane 11, 11' or 11" or member 15, 15' or 15" to resilient portion 14, 14' or 14", see FIGS. 3, 7 and 11. When two struts 20 are used they may spread apart relative to each other so the two struts 20 are closer to one another at the resilient portion 14, 14', 14" or 14'" than at the sides 21, 21' or 21". In FIG. 15 the resilient portion 14'" has two struts 20 without any member or flexible membrane therebetween. The simplicity of this arrangement may make it the most preferred embodiment. That resilient portion 14'" has merely two struts 20 spaced apart to spread the midurethral lumen and remove laxity.

The flexible membrane 11, 11' or 11" or the member 15, 15' or 15" is preferably arcuate or bowed for added resilience along the edge 19, 19' or 19" transverse to the opposite sides 21, 21' or 21" for forming the flexible membrane 11, 11' or 11" to bear against the midurethral walls. The flexible membrane 11, 11' or 11" may be formed of a mesh as shown in FIG. 3. The opposed major surfaces 17, 17' or 17" might perhaps be concave and convex generally in accord with the contour of the midurethral lumen cross section.

The mount 12, 12', 12" or 12'" includes a layer of adhesive 22, 22' or 22" applied thereto and the adhesive is adapted to releasably attach to the female body. The adhesive 22, 22', 22" or 22'" is biocompatible and resistant to perspiration and body oils. FIGS. 2, 3, 4 and 6 show a handle 23 for use in removal of the female incontinence augmentor 10, 10', 10". Similarly, handle 23 could be added to the other embodiments. In FIGS. 1, 2, 5, 6, 7, 8, 10, 11, 12, 14, 15, 16 and 19 an opening 24 is shown to permit the flow of urine during voiding.

A method of making the female continence augmentor 10, 10', 10" or 10'" adapted to prevent involuntary urine loss and improve urethral coaptation by increasing mid-urethral resistance to opening the lumen. The method of making has the steps of forming the mount 12, 12', 12" or 12'" of resilient material including the resilient portion 14, 14 or 14" carried thereon for extending into but not blocking the urethra for at least urging the dorsal midurethral wall in a dorsal direction toward the vagina for stretching and/or reshaping the midurethral lumen to have a more arcuate shape transversely thereacross. The method of making has the steps of connecting the intralumenal part 13, 13', 13" or 13'" to the mount 12, 12', 12" or 12'" and locating the one or more struts 20 for supporting the flexible membrane 11, 11' or 11" or the member 15, 15' or 15". The method has the step of extending the one or more struts 20 from the resilient portion 14, 14' or 14" in position for placement and support of the flexible membrane 11, 11' or 11" or the member 15, 15' or 15" intralumenally. The method of making includes the step of molding the mount 12, 12', 12" or 12'" of a polymer material. The method of making has the step of locating two struts 20 in the midurethral lumen. The method of making has the steps of adding adhesive 22, 22', 22" or 22'" to the mount 12, 12', 12" or 12'" and having biocompatible material 16, 16' or 16" on the member 15, 15' or 15" to improve coaptation.

A method of using the female continence augmentor 10, 10', 10" or 10'" with its mount 12, 12', 12" or 12'" connected to intralumenal part 13, 13', 13" or 13'". The method of using includes the steps of inserting the intralumenal part 13, 13', 13" or 13'" into the urethra so that the flexible membrane 11, 11' or 11", the member 15, 15' or 15" or the two struts 20 thereon are within the midurethral lumen. The step of placing the mount 12, 12', 12" or 12'" adjacent to the urethral exit to retain the member 15, 15' or 15" in the midurethral lumen can be performed. Stretching and/or reshaping the inside of the urethra with the flexible membrane 11, 11' or 11", the member 15, 15' or 15" or the two struts 20 by their connection with resilient portion 14, 14', 14" or 14'" that is connected between the mount 12, 12', 12" or 12'" and member 15, 15' or 15" is a step. The method of using includes steps of urging the dorsal midurethral wall in a dorsal direction for stretching and/or reshaping the midurethral lumen to have a more arcuate shape transversely thereacross. The step of engaging the urethral wall, especially the midurethral wall to remove laxity therein enhances coaptation and increases urethral resistance to opening. The patient may void voluntarily without requiring conscious action to operate the female continence augmentor 10, 10', 10" or 10'" so there is no need to remove, activate, inactivate, alter, it. Following voiding, the female continence augmentor 10, 10', 10" or 10'" resumes functioning automatically.

Figure 20:
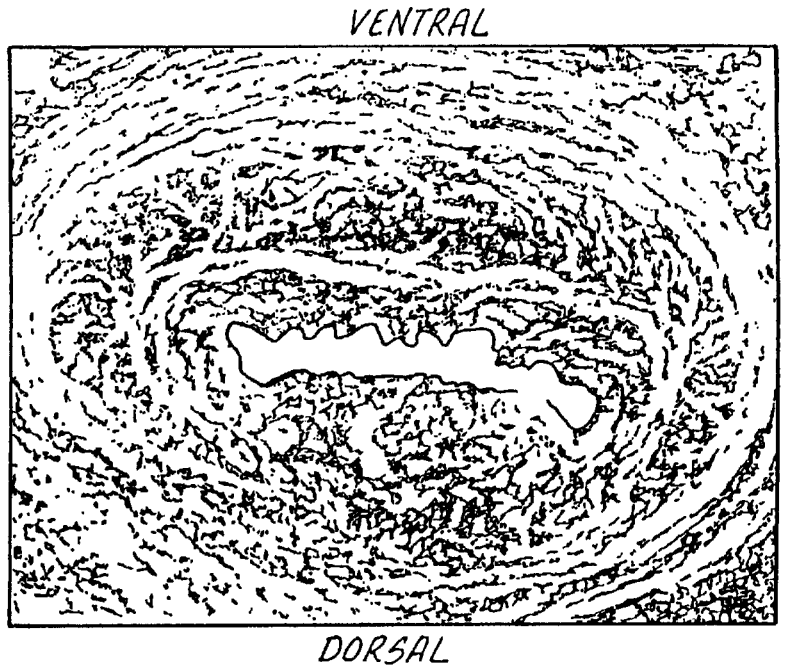
FIG. 20 is a view shown in cross section through the midurethral lumen of a female.
Figure 21:
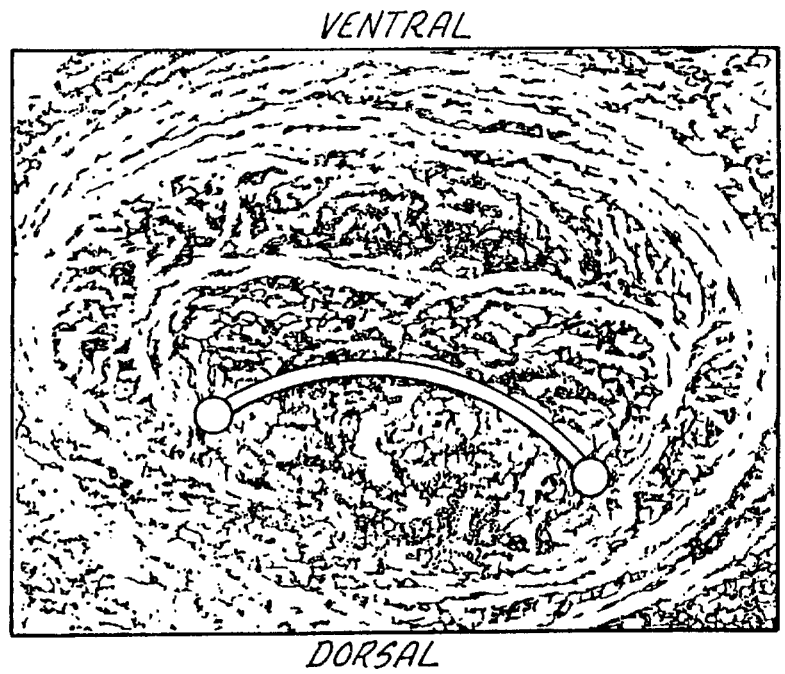
FIG. 21 is a view in cross section through the midurethral lumen of a female and is similar to the view in FIG. 20 however the female continence augmentor is shown in situ.

FIG. 20 is a view shown in cross section through the urethral lumen of a female. Note the irregular arcuate passage of the urethral lumen. FIG. 21 is a view in cross section through the urethral lumen of a female and is similar to the view in FIG. 20 however the female continence augmentor is shown in situ. Note that in FIG. 21 the laxity of the urethral lumen has been alleviated by the incontinence augmentor 10, 10', 10" or 10'". While a preferred embodiment and alternatives have been shown and described, the female continence augmentor 10, 10', 10" or 10'" sought to be protected by the claims that follow stretches and/or reshapes the midurethral lumen cross section.

What is claimed is:

1. A device for improving urinary control in a patient comprising:
   a resilient, shape-inducing structure adapted for internal placement in the urethra of a patient;
   said resilient, shape-inducing structure having a configuration that induces a cross-section of said urethra to assume an elongated shape;
   said resilient, shape-inducing structure having a resiliency not less than the resiliency required to increase a resistance of said urethra to dilation by pressurized urine; and
   a platform upon which said resilient, shape-inducing structure is disposed.

2. The device of claim 1 wherein said resilient, shape-inducing structure is sized to extend from said platform to a mid-urethral region of said urethra.

3. The device of claim 1, wherein said resilient shape-inducing structure is generally rectangular in shape with an arcuate cross-section.

4. The device of claim 3, wherein said resilient shape-inducing structure includes edges which are beveled.

5. The device of claim 1, wherein said shape-inducing structure extends outwardly substantially perpendicular from said platform.

6. The device of claim 1, wherein said platform further comprises a handle.

7. A method of improving urinary control in a human comprising:
   positioning an incontinence member through an opening of a urethra of said human, said incontinence member having an arcuate cross-section;
   using said incontinence member to cause a cross-sectional shape of said urethra to change such that resistance to dilation of said urethra as a result of bladder fluid pressure is increased;

maintaining said change in said cross-sectional shape of said urethra without further manipulation of said incontinence member to prevent involuntary voiding; and allowing said human to void voluntarily without altering said arcuate cross-section of said incontinence member.

8. A method according to claim 7, wherein said change in cross-sectional shape occurs in a mid-urethral region of said urethra.

9. A method according to claim 8, wherein said incontinence member causes said urethra to change into a substantially elongated cross-sectional shape.

10. A method according to claim 9, wherein said substantially elongated shape includes a curved cross-sectional shape.

11. A method according to claim 7, wherein said incontinence device is insertable without surgery.

12. A method according to claim 8, wherein said incontinence device includes a shape-inducing structure for contacting said urethra.

13. A method of improving urinary control in a human comprising:

locating an incontinence device within a urethra of a patient;

using said incontinence device to improve coaptation of mating walls of said urethra;

maintaining the improved coaptation of said mating walls of said urethra when the patient is not voiding; and, voiding through said urethra by overcoming the improved coaptation otherwise being maintained.

14. A method according to claim 13, wherein said improved coaptation is located at a mid-urethral region of said urethra.

15. A method according to claim 13, wherein maintaining the improved coaptation is achieved with an incontinence device having a flexible membrane sized for placement in said urethra.

16. A method according to claim 13, wherein maintaining the improved coaptation is achieved with an incontinence device having at least one flexible strut sized for placement in said urethra.

17. A method according to claim 13, wherein said improved coaptation is achieved by causing an elongation in a cross-sectional shape of said urethra.

18. A method according to claim 17, wherein said elongated cross-sectional shape includes a curved shape.

* * * * *